United States Patent
Hofmann

(10) Patent No.: US 9,585,785 B2
(45) Date of Patent: Mar. 7, 2017

(54) OCCLUSION SPLINT ARRANGEMENT

(76) Inventor: Konrad Hofmann, Thungersheim (DE)

( * ) Notice: Subject to any disclaimer, the term of this patent is extended or adjusted under 35 U.S.C. 154(b) by 176 days.

(21) Appl. No.: 14/387,622

(22) PCT Filed: Mar. 26, 2012

(86) PCT No.: PCT/DE2012/000314
§ 371 (c)(1),
(2), (4) Date: Feb. 17, 2015

(87) PCT Pub. No.: WO2013/143511
PCT Pub. Date: Oct. 3, 2013

(65) Prior Publication Data
US 2015/0157491 A1 Jun. 11, 2015

(51) Int. Cl.
*A61F 5/56* (2006.01)

(52) U.S. Cl.
CPC .................. *A61F 5/566* (2013.01)

(58) Field of Classification Search
CPC ...... A61F 5/56; A61F 5/566; A61F 2005/563; A61F 2002/2864; A61F 2002/488; A61F 2007/0017; A61F 2007/0054; A61F 2007/0075; A61F 5/0006; A61F 7/03; A63B 71/085; A63B 2071/086; A63B 2209/00; A61C 5/007; A61C 13/0004;
(Continued)

(56) References Cited

U.S. PATENT DOCUMENTS 4,376,628 A * 3/1983 Aardse ................ A61C 19/063
128/861
6,516,805 B1 2/2003 Thornton
(Continued)

FOREIGN PATENT DOCUMENTS

| DE | 103 41 260 A1 | 4/2005 |
| DE | 11 2009 001742 T5 | 7/2011 |
| JP | 2002519137 A | 7/2002 |

OTHER PUBLICATIONS

English Language Translation of the International Preliminary Report on Patentability, Application No. PCT/DE2012/000314, Oct. 2, 2014, 7 pages.
(Continued)

*Primary Examiner* — Michael Brown
(74) *Attorney, Agent, or Firm* — Quarles & Brady LLP

(57) ABSTRACT

An occlusal splint arrangement, in particular for sleep apnea therapy includes a maxillary miniplast splint that can be arranged on the maxillary row of teeth and a mandibular miniplast splint that can be arranged on the mandibular row of teeth. The maxillary miniplast splint can be brought to bear against the mandibular miniplast splint. The arrangement includes at least one maxillary positioning guide and at least one mandibular positioning guide, wherein the relative position of the miniplast splints toward each other can be defined in the longitudinal direction and/or in the transverse direction by a form fit between the maxillary and the mandibular positioning guides. The maxillary and/or mandibular miniplast splint include at least one mounting device, and at least two different positioning guides can be secured as mutual replacements on the same mounting device, whereby at least two different relative positions can be defined between the miniplast splints.

10 Claims, 5 Drawing Sheets

(58) Field of Classification Search
CPC ............ A61C 13/0013; A61C 13/0019; A61C 13/082; A61C 8/0006; A61C 8/0012; A61C 8/0018; A61C 8/0036; A61C 8/0075; A61C 9/0046; A61C 7/36; A61C 1/084; A61C 7/08
USPC .......................... 128/848, 859–862; 602/902
See application file for complete search history.

(56) References Cited

U.S. PATENT DOCUMENTS

| | | | |
|---|---|---|---|
| 6,729,335 B1* | 5/2004 | Halstrom | A61F 5/566 128/848 |
| 2005/0028826 A1 | 2/2005 | Palmisano | |
| 2011/0005526 A1* | 1/2011 | Garabadian | A61F 5/566 128/848 |
| 2011/0155144 A1 | 6/2011 | Tousssaint | |
| 2013/0309628 A1* | 11/2013 | Orth | A61C 1/084 433/75 |

OTHER PUBLICATIONS

Japan Patent Office, Notice of Reasons for Refusal, Application No. 2015-502089, Mar. 9, 2016.
International Search Report under date of mailing of Nov. 14, 2012 in connection with PCT/DE2012/000314.

* cited by examiner

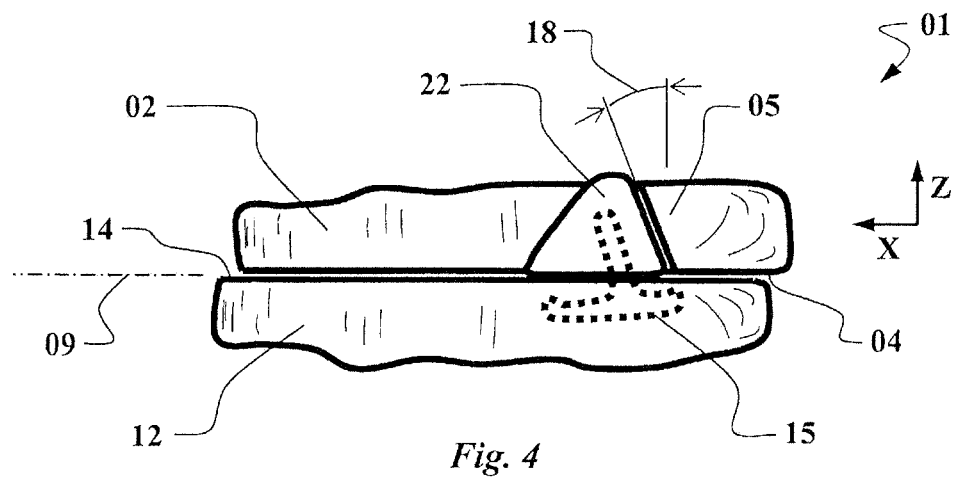
*Fig. 4*
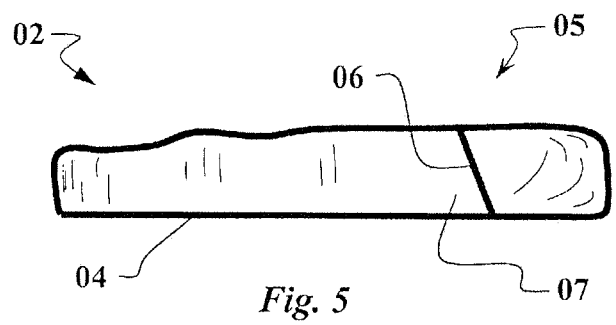
*Fig. 5*
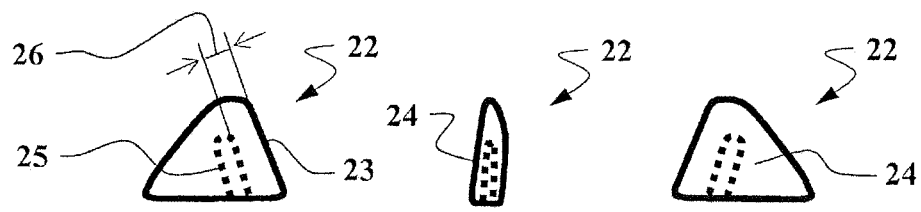
*Fig. 6a*   *Fig. 6b*   *Fig. 6c*
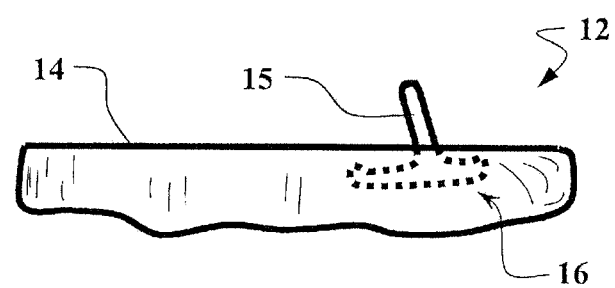
*Fig. 7*

OCCLUSION SPLINT ARRANGEMENT

CROSS-REFERENCE TO RELATED APPLICATIONS

This application represents the national stage entry of PCT International Patent Application No. PCT/DE2012/000314 filed Mar. 26, 2012, which is incorporated herein by reference for all purposes.

STATEMENT REGARDING FEDERALLY SPONSORED RESEARCH OR DEVELOPMENT

Not applicable.

FIELD OF THE INVENTION

The invention relates to an occlusal splint arrangement, in particular for sleep apnea therapy, comprising a maxillary and a mandibular miniplast splint.

BACKGROUND OF THE INVENTION

In particular for sleep apnea therapy, various embodiments of occlusal splint arrangements are known from the state of the art. They basically aim at influencing the position of the upper jaw relative to the lower jaw so that the lower jaw, the tongue muscle and the soft palate are restricted to an appropriate degree from sinking backwards so as to keep the airways open.

An embodiment that is particularly suited for this purpose is disclosed in document DE 103 41 260 A1. The embodiment comprises a maxillary miniplast splint and a mandibular miniplast splint which can each be plugged onto the corresponding rows of teeth. Moreover, the miniplast splints have opposing contact surfaces so that they can be brought to bear against each other. To realize the required relative position of the miniplast splints toward each other, one miniplast splint comprises an adjusting device including a locking pin and the other miniplast splint has a complementary locking guide. The position of the mandibular miniplast splint relative to the maxillary miniplast splint is defined in that the locking pin engages into the locking guide.

Further, the afore-mentioned document has an adjusting device as well as alternative embodiments. The individual position of the mandibular miniplast splint relative to the maxillary miniplast splint can be influenced by the adjusting device. In the cited case, this is achieved in that the position of the locking pin in the adjusting device can be adjusted using an adjusting screw.

Although a reliable positioning between the maxillary and the mandibular miniplast splint for therapy of the sleep apnea syndrome is made possible by known embodiments from the state of the art, the latter per se each still have various disadvantages. On the one hand, they relate to the unnecessarily complex structure and the associated high production costs. Further, the susceptibility to the deposition of dirt is especially disadvantageous in spots that are hard to clean, thus being problematic from a hygienic point of view and requiring a corresponding chemical cleaning after each use.

US 2011/0155144 A1 describes an occlusal splint arrangement in which the mandibular and the maxillary miniplast splint are connected to each other in an articulated manner via two articulated levers and cannot be separated from each other. Adjustment to the upper and lower jaw takes place by a thermoplastic filler material.

U.S. Pat. No. 6,516,805 B1 describes an occlusal splint arrangement in which the mandibular and the maxillary miniplast splint can be fixed in relation to each other by a downwardly extending fixing protrusion. The fixing protrusion is exchangeably mounted in a guiding groove and is locked with a fixing screw.

US 2005/0028826 A1 describes an occlusal splint arrangement in which the mandibular and the maxillary miniplast splint are provided with removably attached positioning devices positioning the miniplast splints relative to each other. To attach the positioning devices, attachment plates are used that are embedded into the plastic of the miniplast splints and to each of which two circular attachment wires are attached. After the attachment plates have been embedded into the plastic of the miniplast splints, the attachment wires protrude sideways from the miniplast splint, and the positioning devices are plugged onto the attachment wires from the side. The problem therein is that the attachment of the positioning devices to the miniplast splints is not sufficiently secure. Moreover, if a positioning device is pushed off the attachment wires by unconscious jaw movements during sleep, for example, there is the danger that loose positioning device may be swallowed or inhaled, which poses an immense health risk.

SUMMARY OF THE INVENTION

It is the object of the present invention to provide an occlusal splint arrangement in which completely secure positioning becomes possible between the mandibular and the maxillary miniplast splint and at the same time the complexity can be reduced as compared to known embodiments. The object is attained by an occlusal splint arrangement described herein, which serves in particular for sleep apnea therapy. Although the present embodiment of an occlusal splint arrangement is primarily intended to be used for therapy of the sleep apnea syndrome, it is also possible to employ the embodiment according to the invention for another kind of occlusal splint arrangement. In this context, the occlusal splint arrangement can just as well be intended for use in the treatment of malpositions of the teeth or as a bite splint for preventing teeth grinding at night or the like.

The generic occlusal splint arrangement comprises a maxillary miniplast splint that can be arranged on the maxillary row of teeth and a mandibular miniplast splint that can be arranged on the mandibular row of teeth. In correspondence to the intended use, the maxillary miniplast splint can be brought to bear against the mandibular miniplast splint. For positioning of the miniplast splints relative to each other, the maxillary miniplast splint comprises at least one maxillary positioning guide and the mandibular miniplast splint comprises at least one mandibular positioning guide. In this context, the type, design and arrangement of the positioning guides on the miniplast splints are initially immaterial. At least, the positioning of the miniplast splints relative to each other requires a form fit between the maxillary and mandibular positioning guides, whereby the relative position of the miniplast splints toward each other can be defined in a longitudinal direction and/or in a transverse direction.

In this regard, it is also initially immaterial whether the form fit is established outside of the mouth prior to the placement on the rows of teeth by joining the miniplast splints, for example, or whether the form fit only occurs once the miniplast splints sitting on the rows of teeth are brought into contact with each other by the mouth being closed. At least, a corresponding form fit between the positioning guide is accomplished at the latest in that the miniplast splints bear against each other when the teeth are being closed so that the relative position of the miniplast splints toward each other is defined. The relative position can include the longitudinal direction, i.e. a forward and backward extension from the patient's perspective, or alternatively or simultaneously a relative positioning in a transverse direction. In this regard, it further is initially immaterial for the embodiment according to the invention whether a slight play is provided therein.

With regard to the mentioned directions, it is to be explained that, from the patient's perspective, the longitudinal direction extends along a line from the back to the front, while the vertical direction is located approximately perpendicular to the occlusal plane and the transverse direction further lies correspondingly vertical to the vertical direction and vertical to the longitudinal direction, i.e. it extends from the left to the right (and vice versa) from the patient's point of view.

According to the invention the required object is attained in that the maxillary and/or mandibular miniplast splint comprises at least one mounting device. In contrast to known embodiments from the state of the art, however, the positioning guide is now designed such that it can be secured to the mounting device present on the miniplast splint. To allow for different relative positions between the mandibular and the maxillary miniplast splint, it is further provided according to the invention that the positioning guide secured to the mounting device can be replaced by another positioning guide that deviates geometrically. Advantageously, each positioning guide that is intended for being secured to the mounting device can effect an individual relative position of the miniplast splints toward each other.

In correspondence to the possibility of exchanging the positioning guide secured to the mounting device, the unavoidable result is that likewise only a single positioning guide can be present, which is exchangeable in principle, but no second, different positioning guide is available to replace it.

The basic idea of the present invention is that an adaptation to the relative adjustment no longer takes place using a complex adjusting device, but rather that only the positioning guide is secured in a simple manner to a mounting device and is quickly replaced when required. Thus, the complexity can be reduced to a minimum and an especially easy cleaning is made possible. In this regard, it is in particular no longer necessary to chemically clean the miniplast splints after each use. Instead, it is sufficient in many cases to simply rinse the miniplast splints and to only occasionally subject them to a chemical cleaning.

It is further advantageous in this embodiment that the corresponding positioning guide can be provided once the attending physician or dentist has determined the required relative position. Thus, in case a change of the relative position becomes necessary, the needed positioning guide can simply be sent by mail from the physician to the patient. A faulty adjustment cannot take place and the patient can secure the required positioning guide to the mounting device on his/her own. In contrast, the state of the art requires an adjustment by the attending physician or dentist so that a change of the relative position by the patient without a visit to the respective physician or dentist is practically impossible. If the adjustment is performed by the respective patient anyways, it is accompanied by a significant risk of faulty adjustment.

According to the invention, the miniplast splints are designed with opposing contact surfaces. This leads to a corresponding bearing of the miniplast splints against each other at the contact surfaces when the teeth are closed. For this purpose, the contact surfaces are preferably arranged in the occlusal plane and here they are advantageously designed to be even, i.e. planar.

For realizing the form fit between the maxillary and mandibular positioning guides so as to produce a defined relative position of the two miniplast splints toward each other in a transverse direction, the maxillary positioning guide, in a particularly advantageous manner, comprises a maxillary guiding surface that extends substantially in the longitudinal direction and approximately in the vertical direction. Analogously, the mandibular positioning guide likewise comprises a mandibular guiding surface that extends substantially in the longitudinal direction and approximately in the vertical direction. In this context, it is particularly advantageous if the guiding surfaces are designed to be complementary to each other. In this way, the form fit between the guiding surfaces and thus between the positioning guides can be realized when the teeth are closed. The relative position can be advantageously defined in the transverse direction by the corresponding orientation of the guiding surfaces, which are basically vertical and approximately parallel to a central plane.

In a further particularly advantageous embodiment, the maxillary positioning guide comprises a maxillary positioning surface that extends substantially in the longitudinal direction and predominantly in the vertical direction. Analogously, the mandibular positioning guide comprises a mandibular positioning surface that extends substantially in the transverse direction and predominantly in the vertical direction. Likewise, it is particularly advantageous to design the positioning surfaces to be complementary to each other. The relative position of the miniplast splints toward each other can consequently be defined in a longitudinal direction by the form fit of the positioning surfaces.

Thus, it is particularly advantageous to design the positioning guides with both guiding surfaces and positioning surfaces. Thus, the relative position of the miniplast splints can be defined in the longitudinal direction and in the transverse direction.

In this regard, it can also be provided that the miniplast splints come into contact, the positioning guides forming a form fit, before the miniplast splints are placed, wherein it is advantageously provided that, first, the miniplast splints are each placed on the corresponding rows of teeth and the form fit occurs only when the teeth are being closed. In this context, it is initially immaterial whether the form fit and thus the relative position occur upon a beginning closing of the teeth or just finally once the miniplast splints bear completely against each other.

With regard to a pleasant wearing comfort of the miniplast splints and to ensuring the required relative position, it is further particularly advantageous if the guiding surfaces are inclined to the outside, deviating from the vertical direction, at an angle of between 1° and 10°. In case of the miniplast splints not corresponding exactly centrically on top of each other in the transverse direction, this inclination of the guiding surfaces ensures that an unhindered closing can still take place upon closing of the teeth and that the guiding surfaces can slide on each other until the teeth are completely closed with a corresponding relative displacement of the miniplast splints into the desired position in the transverse direction.

Likewise, it is particularly advantageous if the positioning surfaces are inclined forward, deviating from the vertical direction, at an angle of between 10° and 40°. Corresponding to the potentially larger deviation of the miniplast splints toward each other in the longitudinal direction when the teeth are open, the corresponding inclination of the positioning surfaces also leads to an advantageous guiding of the miniplast splints toward each other when the teeth are being closed. The direction in which the guiding surface and the positioning surface is to be inclined, deviating from the vertical direction, is obvious to the person skilled in the art when considering the closing possibility of the miniplast splints starting from the open teeth.

According to the invention, the positioning guides are intended to be arranged on the respective miniplast splint at the left and right side in the molar area. This requires at least two positioning guides per miniplast splint have to be present. This is particularly advantageous with regard to the fact that the structural space required for the positioning guides or the space needed in the respective molar area can be taken up without unduly impairing the patient wearing them. In this context, it further is particularly advantageous if the positioning guides are located at the outer side of the row of teeth. Preferably, the positioning guides are located in the area of the cheek between the teeth and the cheek.

In this context, it further is especially advantageous for the use in particular in sleep apnea therapy if the mandibular positioning guide is arranged outside and in front of the maxillary positioning guide. In the case of the advantageous guiding surfaces, the maxillary guiding surface is arranged between the rows of teeth and the mandibular positioning guide, which is consequently arranged between the cheek and the maxillary positioning guide.

The guiding of the mandibular miniplast splint and of the mandibular row of teeth when closing the teeth with a movement relatively forward in relation to the maxillary row of teeth leads to an advantageous arrangement of the mandibular positioning surface in front of the maxillary positioning surface. Thus, likewise, the mandibular miniplast splint can be pulled forward along the positioning surface by closing the teeth if the positioning surfaces are advantageously inclined.

A particularly comfortable way of wearing and also an advantageous embodiment in the sense of a particularly inexpensive solution and of an advantageous cleaning is ensured if the positioning guides are arranged above the occlusal plane and in relation to the respective miniplast splint above the contact surface, respectively. Preferably, the maxillary miniplast splint is arranged with the maxillary positioning guides entirely above the contact surface and above the occlusal plane. In contrast, the mandibular miniplast splint is designed such that its mandibular positioning guide is arranged above the occlusal plane and above the contact surfaces and thus at the level of the maxillary miniplast splint.

A particularly cost-effective implementation and at the same time easy cleaning is ensured if in the occlusal splint arrangement either the maxillary or the mandibular miniplast splint comprises the positioning guides integrally. In the case of two present positioning guides per miniplast splint, the two associated positioning guides are assigned to the respective miniplast splint as an integral component. In this way, production costs can be lowered and, in particular because of the integral structure, no unnecessary joints and cracks can form, which minimizes the deposition of dirt. Further, it is advantageous to choose an integrated structure because it can advantageously influence the stability of the positioning guides on the respective miniplast splint.

Further, it is particularly advantageous if the miniplast splint is correspondingly produced from a single material as a single component. However, this does not apply to embodiments that comprise reinforcing elements, for example, which are embedded in the miniplast splint, such as wire bows, or in which the tooth receptacle for positioning the miniplast splint on the respective row of teeth is formed by a different material than the actual carrier of the miniplast splint, which should integrally comprise at least the positioning guide.

With regard to the positioning guides present according to the invention, which are exchangeable and can replace each other, it is particularly advantageous if they have positioning surfaces that are arranged differently toward each other viewed in the longitudinal direction relative to the mounting device. Preferably, the variation of the relative position of the miniplast splints toward each other can be realized in that the respective positioning guides have corresponding individual distances from the positioning surface to the mounting device. In consequence, switching the positioning guides causes a change of the positioning surfaces and thus a variation of the relative position in the longitudinal direction.

For the implementation of the mounting device it is intended according to the invention to use a centering pin that is cast into the miniplast splint. In doing so, the centering pin can simultaneously cause a centering of the positioning guides and make available a fastening for the positioning guides. Correspondingly, the exchangeable positioning guide has a centering recess that is complementary to the centering pin for mounting to the miniplast splint. For example, the centering pin can be a blanked sheet metal part, which can be anchored in the miniplast splint by casting, for example.

Corresponding to the design of the positioning guide with a centering recess, the positioning surfaces are designed with different distances to the centering recess so as to realize different relative positions of the miniplast splints toward each other.

Taking into account an inclined positioning surface, and in particular in the case of a slightly inclined guiding surface and of the wearing performance in the mouth to be taken into account, it is intended according to the invention that the exchangeable positioning guide is designed in the shape of a fin. In this case, the latter can come to bear with a bottom side against the contact surface of the associated miniplast splint, wherein at least a portion of a lateral flank forms the guiding surface and at least a portion of a front edge produces the positioning surface.

Taking into account the expected structural size of the miniplast splints and the available space usable without impairing comfort, it is particularly advantageous if the exchangeable positioning guide has a height of between 5 mm and 30 mm above the contact surface, in particular of between 12 mm and 18 mm. In this context, the exchangeable positioning guide can protrude slightly beyond the respectively other miniplast splint. In this way, a reliable guiding and a reliable form fit between the maxillary and the mandibular positioning guides are ensured.

The shaping of the guiding surface is initially immaterial as long as a corresponding form fit when closing the teeth and an association of the miniplast splints on top of each other is possible. In this regard, the guiding surface can be curved or plane. Taking into account the regular shaping of miniplast splints and the arrangement of the positioning guides on the miniplast splints and taking into account a slight inclination deviating from the vertical direction, the guiding surfaces are to be designed preferably mainly even or with a very slight curvature.

The design of the positioning surfaces is also initially immaterial as long as a corresponding form fit between the positioning surfaces is possible when closing the teeth. The positioning surfaces can be designed to be curved or also plane. In a curved embodiment of the positioning surfaces, if the relative position of the miniplast splints in the longitudinal direction does not exactly coincide, a closing movement of the teeth will generally lead to an initially forward-rushing and finally slower forward motion of the positioning guides correspondingly lying in front together with the associated miniplast splint. However, the more complex shaping is disadvantageous for realizing complementary shapes between the mandibular and maxillary positioning surfaces, in particular when taking into account the exchangeability of the positioning guides. In consequence, a plane design is particularly suited in this case.

In the following figures, an advantageous embodiment of an occlusal splint arrangement according to the invention and possible variations for the exchangeable positioning guides will be outlined.

BRIEF DESCRIPTION OF THE DRAWINGS

In the figures:

FIG. 4 shows the occlusal splint arrangement of FIG. 1 in a lateral view;

FIG. 5 shows the maxillary miniplast splint of FIG. 4;

FIGS. 6a, 6b, and 6c show the exchangeable positioning guide for FIG. 4;

FIG. 7 shows the mandibular miniplast splint for FIG. 4;

DETAILED DESCRIPTION OF THE EXAMPLE EMBODIMENTS

Figure 1:
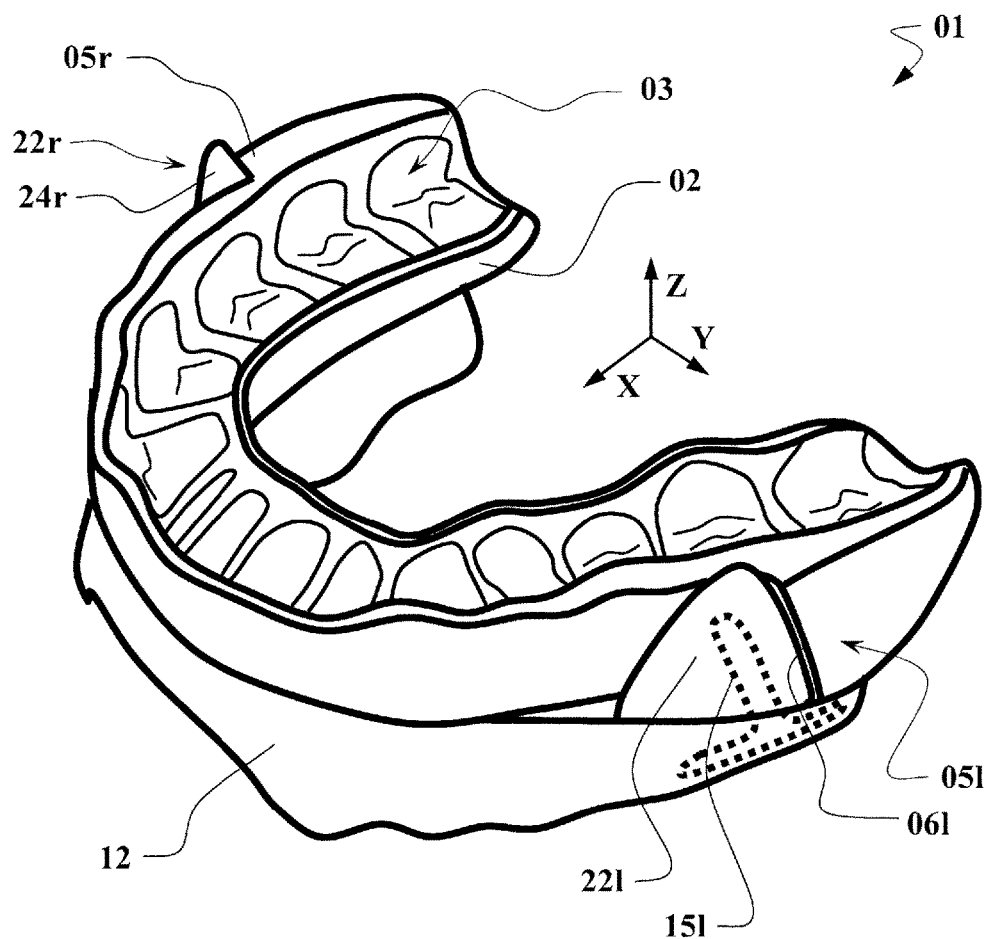
FIG. 1 shows an exemplary embodiment of an occlusal splint arrangement according to the invention in a perspective view.

In FIGS. 1-8, an exemplary occlusal splint arrangement is outlined. The structure with the maxillary miniplast splint 02 and with the mandibular miniplast splint 12 on the lower side is visible. The maxillary miniplast splint 02 comprises a corresponding teeth receptacle 03 for arrangement on the maxillary row of teeth. Analogously, the mandibular miniplast splint 12 correspondingly comprises a teeth receptacle 13 (lying covered below) for arrangement of the mandibular miniplast splint 12 on the mandibular row of teeth. Each of the miniplast splints 02, 12 comprises a positioning guides 05 and 22, respectively, on both sides in the molar area. It is already recognizable that the maxillary positioning guides 05r on the right side and 05l on the left side form an integral component of the maxillary miniplast splint 02. The mandibular positioning guide 22, on the other hand, is designed as an exchangeable positioning guide 22r for the right side and 22l for the left side. In each case, it is mounted on a mounting device in the form of a centering pin 15r and 15l, respectively.

Each of the positioning guides 05, 22 has guiding surfaces 07, 24. They serve to center and guide the miniplast splints 02, 12 relative to each other in the transverse direction (Y). The positioning in the longitudinal direction (X) is accomplished with the opposing positioning surfaces 06 and 23.

Figure 2:
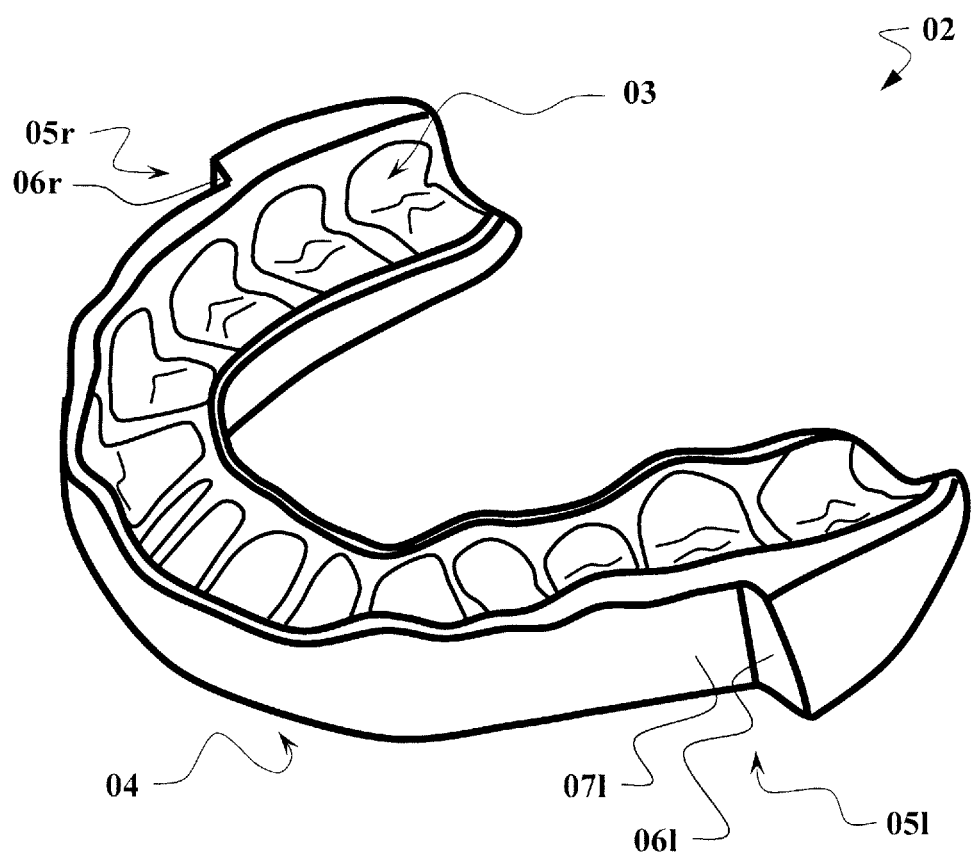
FIG. 2 shows the maxillary miniplast splint for the design of FIG. 1.

In FIG. 2, the maxillary miniplast splint 02 is outlined once more in this regard. Again, the arrangement of the teeth receptacle 03 for placement of the maxillary miniplast splint 02 on the patient's maxillary row of teeth is visible. Further, the positioning guides 05r and 05l in the molar area are visible, each with a guiding surface 07 and a positioning surface 06. The contact surface 04 is located on the bottom side (lying covered), which in this case has an even shape and is intended to bear against the respective other miniplast splint 12.

Figure 3:
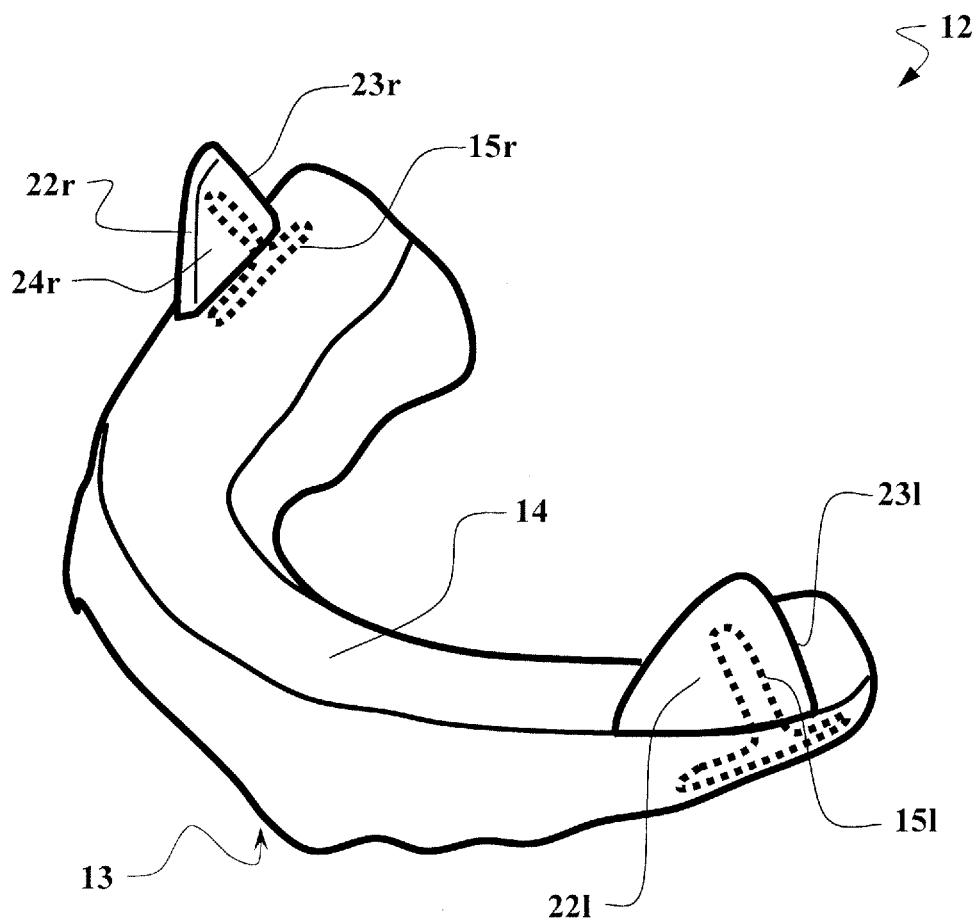
FIG. 3 shows the mandibular miniplast splint for the design of FIG. 1.

FIG. 3 outlines the mandibular miniplast splint 12 of FIG. 1, in which the teeth receptacle 13 is positioned at the bottom (covered)(as in FIG. 1). The illustrated top side forms the contact surface 14, which is also formed even and is intended to abut against the maxillary contact surface 04 of the maxillary miniplast splint 02.

The relative position between the miniplast splints 02, 12 is accomplished in this case by the exchangeable positioning guides 22r, 22l, each of which has a guiding surface 24, which is complementary to the maxillary positioning guide 05, and a corresponding complementary positioning surface 23. Further, the outlined manner of attachment of the positioning guide 22 on the mandibular miniplast splint 12 is visible, which takes place by the centering pins 15l, 15r that are anchored in the base body of the miniplast splint. In this case, the exchangeable positioning guide 22 appears in the manner of a fin, in which the surface facing toward the center forms the guiding surface 24 and the front edge of the fin lying toward the rear forms the positioning surface 23.

In FIG. 4, again, the occlusal splint arrangement 01 of FIG. 1 is outlined in the lateral view. The arrangement of the contact surfaces 04 of the maxillary miniplast splint 02 opposite of the contact surface 14 of the mandibular miniplast splint 12 is visible, the contact surfaces 04 substantially lying in the occlusal plane 09 when the teeth are closed. Here, it can further be seen that the maxillary positioning guide 05 of the maxillary miniplast splint 02 is located entirely above the contact surface 04, whereas the mandibular positioning guide 22 is arranged above the corresponding contact surface 14 on the mandibular miniplast splint 12. Further, the design of the positioning surfaces 06, 23 is visible, which are designed basically even, but inclined forward with respect to the vertical direction (Z). Further (comp. FIG. 1), it is to be taken into account that the mandibular positioning guide 22 is located outside and in front of the maxillary positioning guide 05. In this manner, it is ensured for effective sleep apnea therapy that the mandibular miniplast splint 12 and thus the lower jaw is pulled forward when the teeth are closed.

In FIG. 5, additionally to FIG. 4, the maxillary miniplast splint 02 is outlined again in the lateral view, with the positioning surface 06 oriented in the transverse direction (Y) and in the vertical direction (Z) and the guiding surface 07 of the maxillary positioning guide 05 oriented in the longitudinal direction (X) and in the vertical direction (Z).

In addition to FIG. 4, FIGS. 6a, 6b, ad 6c outline the exchangeable positioning guide 22 in the manner of a fin with a centering recess 25 for placement of the positioning guide 22 on a correspondingly associated centering pin 15. Herein, a lateral surface of the fin as the positioning guide 22 forms the guiding surface 24, a front edge of the fin forming the positioning surface 23 of the positioning guide 22. Also visible is the distance 26 between the positioning surface 23 and the centering recess 25, which 26 is crucial for determining the relative position of the two miniplast splints 02, 12 toward each other.

In addition to FIG. 4, FIG. 7 shows the mandibular miniplast splint 12, but without its associated positioning guide 22. The mounting device is visible as a centering pin 15, which protrudes beyond the contact surface 14 and is embedded with an anchor 16 in the miniplast splint 12.

Figure 8:
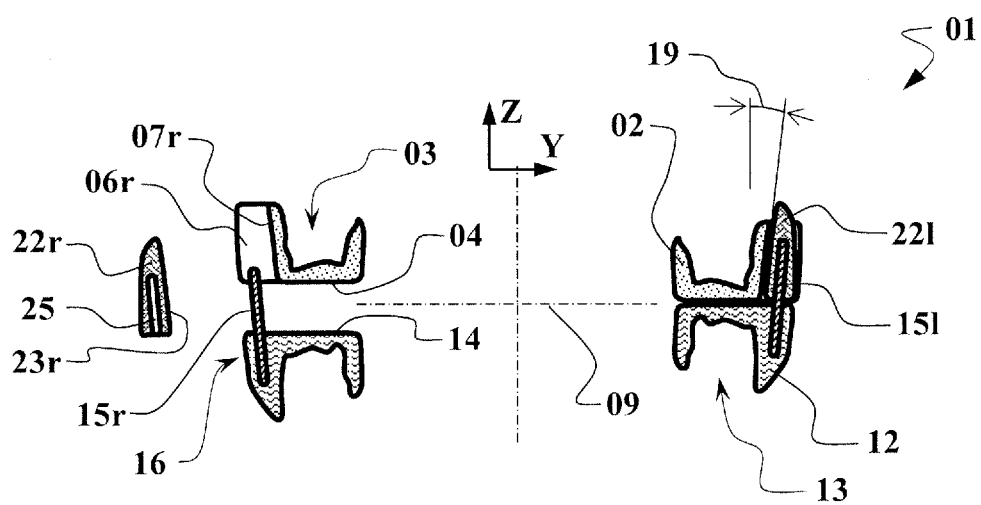
FIG. 8 shows a cut through the occlusal splint arrangement of FIG. 1.

Additionally, FIG. 8 outlines a cut through the occlusal splint arrangement 01, wherein the latter is outlined in an exploded illustration on the left side and in a position one on top of the other on the right side. Again, the arrangement of the maxillary miniplast splint 02 with the maxillary teeth receptacle 03 and, on the opposite side, the mandibular miniplast splint 12 with the corresponding teeth receptacle 13 is visible. Each of the miniplast splints 02, 12 has corresponding contact surfaces 04, 14, respectively, which come to bear against each other in the occlusal plane 09 when the teeth are closed. The relative guiding in the transverse direction (Y) is ensured by the guiding surfaces 07 in contact with the guiding surfaces 24. The guiding surfaces 07, 24 are inclined to the outside with regard to the vertical direction (Z) by an angle of inclination 19. Thus, it is ensured that the guiding surfaces 07, 24 find each other when the teeth are being closed, without the mandibular positioning guide 22 colliding with the contact surface 04 of the maxillary miniplast splint 02.

Further, the manner of attachment of the exchangeable positioning guide 22 to the mandibular miniplast splint 12 by placing the centering recess 25 on the centering pin 15 is visible.

Figure 9A:
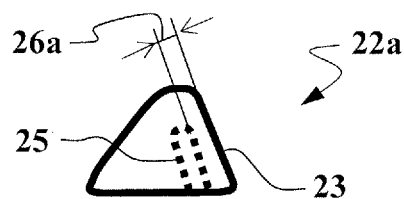
FIGS. 9a, 9b, and 9c show different positioning guides for different relative positions.
Figure 9B:
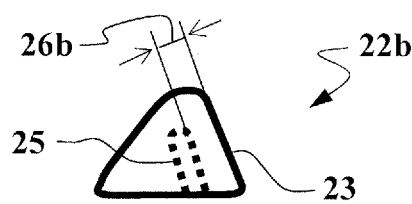
Figure 9C:
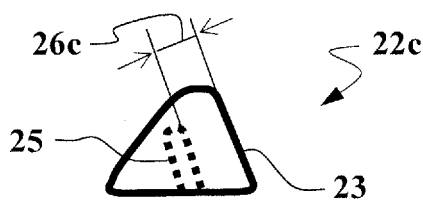

FIG. 9 now outlines the possibility of relative arrangement between the maxillary miniplast splint 02 and the mandibular miniplast splint 12, which is substantial to the invention. Herein, the relevant distance 26 between the positioning surface 23 and the centering recess 25 on positioning guides 22a, 22b, and 22c is varied in each case, with a small distance 26a in FIG. 9a, a medium distance 26b in FIG. 9b and a larger distance 26c in FIG. 9c.

Figure 10U:
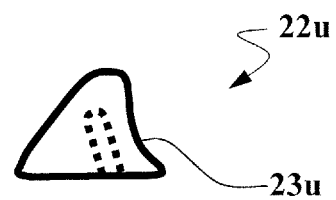
FIGS. 10u, 10v, and 10w show alternative embodiments of the positioning surface.
Figure 10V:
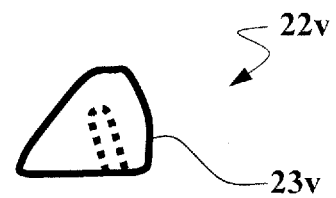
Figure 10W:
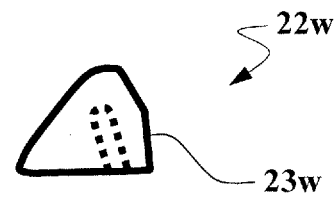

Finally, FIGS. 10u, 10v, and 10w outline alternative embodiments for the positioning surface 23 of positioning guides 22u, 22v, and 22w, wherein it is obvious that the complementary positioning surface 26 should have a corresponding shape. The concave shape of the positioning surface 23u is visible in FIG. 10u, the convex positioning surface 23v in FIG. 10v and an angled positioning surface 23w in FIG. 10w.

The invention claimed is:

1. An occlusal splint arrangement for sleep apnea therapy, the occlusal splint arrangement comprising:
    a maxillary miniplast splint arrangeable on a maxillary row of teeth; and
    a mandibular miniplast splint arrangeable on a mandibular row of teeth, wherein the maxillary miniplast splint can be brought to bear against the mandibular miniplast splint, and wherein the miniplast splints include even contact surfaces that substantially oppose each other in an occlusal plane having at least one maxillary positioning guide and at least one mandibular positioning guide, wherein the relative position of the miniplast splints toward each other is definable in a longitudinal direction and/or in a transverse direction by a form fit between the maxillary and the mandibular positioning guides, and wherein each miniplast splint includes one positioning guide arranged on one side in a molar area and another positioning guide on another side in the molar area,
    and wherein the maxillary and/or mandibular miniplast splint includes at least one centering pin, wherein at least two different positioning guides on the same miniplast splint are alternatively securable to the centering pin of the same miniplast splint, whereby at least two different relative positions are definable between the miniplast splints,
    and wherein the alternatively securable positioning guides are exchangeable, each exchangeable positioning guide having a centering recess that is complementary to the centering pin for mounting to the miniplast splint, and each exchangeable positioning guide being attachable by placing the centering recess on the centering pin, and the centering pin simultaneously allowing a centering of the exchangeable positioning guide and an attachment of the exchangeable positioning guide, and the exchangeable positioning guide being formed in the shape of a fin, a bottom side of the fin coming to bear on the contact surface of the associated miniplast splint and a portion of a lateral flank of the fin forming the guiding surface and a portion of a front edge of the fin forming the positioning surface,
    wherein the centering pin is anchored by being cast into the miniplast splint and protrudes beyond the contact surface.

2. The occlusal splint arrangement according to claim 1, wherein the maxillary positioning guide has a maxillary guiding surface that extends substantially in the longitudinal direction and approximately in the vertical direction, and the mandibular positioning guide has a complementary mandibular guiding surface that extends substantially in the longitudinal direction and approximately in the vertical direction, the relative position of the miniplast splints toward each other being definable in the transverse direction by a form fit of the guiding surfaces.

3. The occlusal splint arrangement according to claim 2, wherein the guiding surface is inclined to the outside deviating from the vertical direction at an angle of between 1° and 10° and/or the positioning surface is inclined forward deviating from the vertical direction at an angle of between 10° and 40°.

4. The occlusal splint arrangement according to claim 1, wherein the maxillary positioning guide has a maxillary positioning surface that extends substantially in the transverse direction and mainly in the vertical direction, and the mandibular positioning guide has a complementary mandibular positioning surface that extends substantially in the transverse direction and mainly in the vertical direction, the relative position of the miniplast splints toward each other being definable in the longitudinal direction by a form fit of the positioning surfaces.

5. The occlusal splint arrangement according to claim 1, wherein the mandibular positioning guide is arranged outside and in front of the maxillary positioning guide.

6. The occlusal splint arrangement according to claim 1, wherein the maxillary and the mandibular positioning guides are arranged substantially above the respective contact surface of the maxillary and mandibular miniplast splint, respectively.

7. The occlusal splint arrangement according to claim 1, wherein the maxillary or the mandibular miniplast splint integrally includes the positioning guide.

8. The occlusal splint arrangement according to claim 1, wherein the exchangeable positioning guides that replace one another have positioning surfaces that are arranged differently to one another in the longitudinal direction relative to the centering pin.

9. The occlusal splint arrangement according to claim 8, wherein the exchangeable positioning guides that replace one another have different distances of the positioning surface to the centering recess.

10. The occlusal splint arrangement according to claim 1, wherein the exchangeable positioning guides have a height above the contact surface of between 12 mm and 18 mm.

* * * * *